(12) United States Patent
Han et al.

(10) Patent No.: US 6,416,797 B1
(45) Date of Patent: Jul. 9, 2002

(54) PROCESS FOR MAKING A WHEYLESS CREAM CHEESE USING TRANSGLUTAMINASE

(75) Inventors: Xiao-Qing Han, Naperville; Jochen Klaus Pfeifer, Evanston; Richard Harold Lincourt, Mundelein, all of IL (US)

(73) Assignee: Kraft Foods Holdings, Inc., Northfield, IL (US)

( * ) Notice: Subject to any disclaimer, the term of this patent is extended or adjusted under 35 U.S.C. 154(b) by 0 days.

(21) Appl. No.: 09/783,227

(22) Filed: Feb. 14, 2001

(51) Int. Cl.[7] ................................................. A23C 9/12
(52) U.S. Cl. ........................ 426/36; 426/34; 426/580; 426/582
(58) Field of Search ............................... 426/34, 36, 38, 426/39, 40, 42, 43, 580, 582, 519

(56) References Cited

U.S. PATENT DOCUMENTS

| | | | |
|---|---|---|---|
| 4,244,983 A | 1/1981 | Baker | 426/582 |
| 4,324,804 A | 4/1982 | Davis | 426/36 |
| 4,341,801 A | 7/1982 | Weissman | 426/40 |
| 4,379,175 A | 4/1983 | Baker | 426/582 |
| 4,390,560 A | 6/1983 | Koide et al. | 426/582 |
| 4,397,878 A | 8/1983 | Koide et al. | 426/40 |
| 4,534,982 A | 8/1985 | Yoshida et al. | 426/36 |
| 4,724,152 A | 2/1988 | Baker et al. | 426/335 |
| 5,156,956 A | 10/1992 | Motoki et al. | 435/68.1 |
| 5,656,320 A | 8/1997 | Cheng et al. | 426/582 |
| 5,681,598 A | 10/1997 | Kuraishi et al. | 426/36 |
| 5,731,183 A | 3/1998 | Kobayashi et al. | 435/193 |
| 5,882,704 A | 3/1999 | Yamaguchi et al. | 426/36 |
| 6,093,424 A | 7/2000 | Han et al. | 426/42 |
| 6,096,352 A * | 8/2000 | Kijowski et al. | 426/36 |
| 6,190,879 B1 * | 2/2001 | Bech et al. | 435/68.1 |
| 6,242,036 B1 * | 6/2001 | Han et al. | 426/582 |

FOREIGN PATENT DOCUMENTS

| | | | | |
|---|---|---|---|---|
| EP | 0 711 504 A1 | 5/1996 | | A23C/19/032 |
| JP | 59-59151 | 4/1984 | | A23J/3/00 |
| JP | 2-276541 | 11/1990 | | A23J/3/00 |
| WO | WO 93/22930 | 11/1993 | | A23C/11/00 |
| WO | WO 94/21129 | 9/1994 | | A23C/9/127 |
| WO | WO 94/21130 | 9/1994 | | A23C/9/127 |
| WO | WO 97/01961 | 1/1997 | | A23C/19/032 |

* cited by examiner

Primary Examiner—Leslie Wong
(74) Attorney, Agent, or Firm—Fitch, Even, Tabin & Flannery

(57) ABSTRACT

The current invention includes a process for making cream cheese wherein nutrients typically lost as whey during processing are utilized in the final cream cheese; the resulting cream cheese has the body, texture, and taste of conventional cream cheese. The process of the current invention utilizes acidifying and cross-linking steps to process a dairy liquid into a wheyless cream cheese by utilizing the protein cross-linking activity of transglutaminase. The wheyless cream cheese does not require the addition of stabilizers and/or emulsifiers. Furthermore, the cream cheese that is formed is firmer than typical cream cheese and has significantly reduced syneresis.

34 Claims, 5 Drawing Sheets

PROCESS FOR MAKING A WHEYLESS CREAM CHEESE USING TRANSGLUTAMINASE

FIELD OF THE INVENTION

The invention relates to the production of cream cheese. More specifically, the invention relates to methods for producing a wheyless cream cheese using transglutaminase.

BACKGROUND

Cheese compositions are generally prepared from dairy liquids by processes that include treating the liquid with a coagulating or clotting agent. The coagulating agent may be a curding enzyme, an acid, or a suitable bacterial culture. The coagulum or curd that results generally incorporates transformed casein, fats (including natural butter fat), and flavorings (especially those arising when bacterial cultures are used). The curd is usually separated from the whey and is then collected. The resulting liquid whey generally contains substantial portions of nutrients, including soluble proteins, mineral salts, and lactose, that are normally lost in the manufacturing process. The inability of whey nutrients to be retained in the coagulum is an important factor contributing to a lack of efficiency in production of cheese curds, and to a reduction in overall yield of protein solids from the starting dairy liquids. Therefore, there remains a need for more effective methods of improving the efficiency of nutrient incorporation during cheese production.

Cream cheese is a mild, acid-coagulated uncured cheese made of dairy components including a fat source (e.g., a mixture of cream and milk). Cream cheese is normally stored under refrigeration conditions (i.e., about 2 to about 8° C.) and typically has a smooth and butterlike body. At refrigeration temperatures, cream cheese can normally be sliced, but it is not soft or readily spreadable and cannot readily be applied to a soft or brittle substrate.

Attempts have been made to develop a process for making wheyless cream cheese in which nutrients traditionally lost in the whey are retained in the cheese product. However, cheese or cheese-like products produced by such processes typically do not have the body, texture, and/or taste desired in cream cheese. Therefore, there remains a need to develop processes for making cream cheese in which the cheese has body, texture, and taste similar to that found in cream cheese prepared by conventional processes (i.e., curds and whey processes).

U.S. Pat. No. 5,882,704 discloses a process for the production of cream cheese-like products in which whey is not removed during the process. The methods disclosed do not include the use of transglutaminase to improve the texture and body of the wheyless cheese produced. Furthermore, the method disclosed uses an emulsifier which adds cost to the process. Moreover, under the current United States Standards of Identity, a product containing such emulsifiers cannot be labeled as cream cheese.

U.S. Pat. No. 4,724,152 discloses a process for the production of cream cheese-like products in which whey is not removed during the process. The methods disclosed in this patent do not include the use of transglutaminase to improve the texture and body of the wheyless cheese produced. Furthermore, the methods disclosed uses stabilizers which increases the cost of processing using the disclosed method. Moreover, in some countries, a product containing stabilizers cannot be labeled as cream cheese; in the United States, the Standards of Identity limit the total amount of stabilizers to less than 0.5 percent for cream cheese.

In addition to inefficiencies in nutrient utilization during production, cream cheeses also lose nutrients during storage as a result of syneresis (i.e., water separation). Acid whey generated by syneresis, although it contains substantial amounts of dairy proteins, cannot be efficiently utilized. Moreover, consumers generally consider syneresis to be a product defect. Therefore, there remains a need for improved methods for producing cream cheeses wherein syneresis is reduced.

Transglutaminases are enzymes which catalyze the cross-linking of proteins. These enzymes have a broad occurrence in nature and may be obtained, for example, from microorganisms such as those belonging to the genus Streptoverticillium or from *Bacillus subtilis*, from various Actinomycetes and Myxomycetes, from fish and other marine sources, from plant sources, and from animal sources (especially mammals).

Food processing methods employing transglutaminase have been disclosed in recent years. For example, Japanese Patent 59059151 discloses treating an emulsion containing proteins, oils or fats, and water with transglutaminase to produce a gelatinous, cross-linked gel. However, the cross-linked gel does not have the texture, body, and/or taste of cream cheese. Japanese Patent 02276541 discloses a heat-resistant food protein having a fiber texture prepared by treatment of a protein hydrogel with a transglutaminase in the presence of calcium ions to induce cross-linking of the surfaces of fiber bundles. However, the heat resistant food protein does not have the texture, body, and/or taste of cream cheese.

U.S. Pat. No. 5,156,956 discloses a transglutaminase purified from strains of the genus Streptoverticillium, and the use of this enzyme to produce gel type foods. This transglutaminase catalyzes formation of protein gelation products from protein solutions to produce conventional gel foodstuffs such as yogurt, jelly, cheese, gel cosmetics, and the like. No methods are disclosed in this patent for using transglutaminase to produce cream cheese or to use transglutaminase to produce cheese without forming a gel. Furthermore, methods are not disclosed in this patent for both acidifying a dairy liquid and cross-linking proteins in the dairy liquid.

U.S. Pat. No. 5,731,183 discloses a transglutaminase purified from strains of *Bacillus subtilis*, having particular physical and enzymatic characteristics, and a method for producing protein, peptide, or non-protein amino acid polymers that are cross-linked via their glutamine and lysine residues to form intermolecular or intramolecular conjugates. Although transglutaminase is disclosed as being used in cross-linking protein polymers for use in a variety of food substances, no methods are disclosed for using transglutaminase to produce cheese.

Methods have been proposed for increasing the recovery of whey protein into cheese products using transglutaminase. For example, U.S. Pat. No. 6,093,424 relates to treatment of a dairy liquid such as milk with transglutaminase and a non-rennet protease to generate cheese curd for hard, soft, or semi-soft cheeses. The disclosed methods do not use transglutaminase to produce wheyless cheese; nor do the methods use an acidifying agent, such as a lactic acid producing culture, for making a cheese.

U.S. Pat. No. 5,681,598 and its European counterpart EP 0 711 504 A1 disclose a process for producing cheese using transglutaminase added to milk at a concentration of at least one international unit (IU) transglutaminase per gram milk protein. The transglutaminase is added at the same time as a clotting enzyme and a lactic-acid producing culture; the milk is then incubated. This patent does not disclose a process for using transglutaminase for producing wheyless cheese. Patent publication WO 97/01961 discloses a method for producing cheese using transglutaminase. Transglutaminase is added to milk, followed by a short incubation period, after which a clotting enzyme or curding agent is added to the milk to produce curd. WO 97/01961 does not disclose the use of transglutaminase to produce wheyless cheese.

The current invention meets longstanding needs in the art discussed above. For example, the current invention meets the important need of a process for producing cream cheese in which whey nutrients are not lost in the process. Furthermore, the current invention meets the need of providing a process for preparing wheyless cheese having the texture, body, and taste of conventional cream cheese. Finally, the current invention meets the need of a cream cheese product with significantly reduced syneresis.

SUMMARY OF THE INVENTION

The current invention includes a process for making cream cheese wherein nutrients typically lost as whey during processing are utilized in the final cream cheese; the resulting cream cheese has the body, texture, and taste of conventional cream cheese. The process of the current invention utilizes acidifying and cross-linking steps to process a dairy liquid into a wheyless cream cheese by utilizing the protein cross-linking activity of transglutaminase. The wheyless cream cheese does not require the addition of stabilizers and/or emulsifiers. Furthermore, the cream cheese that is formed is firmer than typical cream cheese and has significantly reduced syneresis.

The current invention provides a process for making a wheyless cream cheese, said process comprising:
(1) treating a dairy liquid containing dairy proteins with transglutaminase and a lactic acid producing culture at about 20 to about 40° C. (preferably at about 25 to about 40° C.) until the pH reaches about 4.2 to about 5.2 to cross-link at least a portion of the dairy proteins and to form a first dairy mixture;
(2) homogenizing the first dairy mixture to break up any curd that may have formed and to form a treated dairy mixture;
(3) cooking the treated dairy mixture at about 75 to about 90° C. for about 2 to about 120 minutes (preferably about 10 to about 60 minutes) to form a first blend; and
(4) homogenizing the first blend to form a cream cheese having fat globules with an average diameter of about 0.2 to about 3 microns.

The current invention provides a process for making a wheyless cream cheese, said process comprising:
(1) treating a dairy liquid with transglutaminase at about 40 to about 60° C. for about 2 to about 120 minutes (preferably about 10 to 60 minutes) to cross-link at least a portion of the dairy proteins and to form a treated dairy liquid;
(2) cooking the treated dairy mixture at 75 to about 90° C. for about 2 to about 120 minutes (preferably about 10 to about 60 minutes) to form a first blend;
(3) adjusting the pH of the first blend to about 4.2 to about 5.2 by adding an edible acid; and
(4) homogenizing the pH-adjusted first blend to form the wheyless cream cheese having fat globules with an average diameter of about 0.2 to about 3 microns.

The current invention also provides a process for making a wheyless cream cheese, said process comprising:
(1) blending a dairy liquid containing dairy proteins with transglutaminase and a lactic acid producing culture to form a first dairy mixture;
(2) incubating the first dairy mixture at about 20 to about 40° C. (preferably at about 25 to about 40° C.) until the pH reaches about 4.2 to about 5.2 to cross-link at least a portion of the dairy proteins and to form a second dairy mixture;
(3) homogenizing the second dairy mixture to break up any curd that may have formed and to form a third dairy mixture;
(4) heating the third dairy mixture at about 40 to about 60° C. for about 2 to about 60 minutes to form a treated dairy liquid;
(5) mixing the treated dairy liquid with a wet mix or a treated wet mix to form a first blend;
(6) homogenizing the first blend to form a second blend;
(7) cooking the second blend at a temperature of about 75 to about 90° C. for about 2 to about 120 minutes (preferably about 10 to about 60 minutes) to form a third blend; and
(8) homogenizing the third blend to form a cream cheese having fat globules with an average diameter of about 0.2 to about 3 microns;
wherein the wet mix is prepared by a first method comprising:
(A) blending whey protein, milk protein concentrate, or mixtures thereof in water at a temperature of about 60 to about 75° C. to form a first mixture containing dairy proteins; and
(B) blending fat with the first mixture to form the wet mix; and
wherein the treated wet mix is prepared by a second method comprising:
(A) homogenizing the wet mix;
(B) adding transglutaminase to the homogenized wet mix to form a second mixture; and
(C) incubating the second dairy mixture for a time and temperature sufficient to cross-link at least a portion of the dairy proteins to form the treated wet mix.

The current invention also provides a process for making a wheyless cream cheese, said process comprising:
(1) blending a dairy liquid containing dairy proteins with transglutaminase to form a first dairy mixture;
(2) incubating the first dairy mixture at about 40 to about 60° C. for about 2 to about 120 minutes (preferably about 10 to 60 minutes) to cross-link at least a portion of the dairy proteins to form a treated dairy liquid;
(3) mixing the treated dairy liquid with a wet mix or a treated wet mix to form a first blend;
(4) homogenizing the first blend;
(5) cooking the homogenized first blend at about 50 to about 95° C. for about 2 to about 120 minutes (preferably about 10 to about 60 minutes) to form a second blend;
(5) adjusting the pH of the second blend to about 4.2 to about 5.2 by adding an edible acid to form a third blend; and
(6) homogenizing the third blend to form a cream cheese having fat globules with an average diameter of about 0.2 to about 3 microns;
wherein the wet mix is prepared by a first method comprising:
(A) blending whey protein, milk protein concentrate, or mixtures thereof in water at a temperature of about 60 to about 75° C. to form a first mixture containing dairy proteins; and (B) blending fat with the first mixture to form the wet mix; and wherein the treated wet mix is prepared by a second method comprising:

(A) homogenizing the wet mix;
(B) adding transglutaminase to the homogenized wet mix to form a second mixture; and
(C) incubating the second dairy mixture for a time and temperature sufficient to cross-link at least a portion of the dairy proteins to form the treated wet mix.

DESCRIPTION OF THE PREFERRED EMBODIMENTS

The present invention provides an improved process for making cream cheese wherein nutrients typically lost as whey during processing are utilized in the final cream cheese; the resulting cream cheese has the body, texture, and taste of conventional cream cheese. The process of the current invention utilizes acidifying and cross-linking steps to process a dairy liquid into a wheyless cream cheese by utilizing the protein cross-linking activity of transglutaminase. The wheyless cream cheese does not require the addition of stabilizers and/or emulsifiers. Furthermore, the cream cheese that is formed is firmer than typical cream cheese and has significantly reduced syneresis.

In conventional processes for making cream cheese, whey is formed and removed. However, in the present invention, a cream cheese is produced without separation and/or removal of the whey. In accordance with the current Federal Standards of Identity, after processing, the finished cream cheese product should have a butterfat content of at least about 33 percent and a total milk solids content of at least 45 percent (corresponding to no more than 55 percent moisture). However, in the current invention, the term "cream cheese" is intended to cover cream cheese falling within the current Standards of Identity as well as cream cheese-like products falling outside the current Standards of Identity. Such cream cheese-like products prepared in accordance with the present invention have texture, body, and/or taste similar to conventionally prepared cream cheese. Thus, using the present invention, cream cheese-like products may be prepared having butterfat contents less than conventional cream cheese (e.g., about 1 to about 38 percent) while maintaining texture, body, and/or taste similar to, and characteristic of, conventionally prepared cream cheese. Thus, using the present invention, reduced-fat cream cheeses can be prepared having organoleptic characteristics similar to conventionally prepared full-fat cream cheeses.

The present invention uses transglutaminase to cross-link at least a portion of the dairy proteins normally found in dairy liquids. For purposes of this invention, a "treated dairy liquid" is a dairy liquid in which at least a portion of the dairy proteins in the initial dairy liquid have been cross-linked using transglutaminase. The degree of cross-linking should be sufficient to provide the desired textural and protein retention characteristics in the final cream cheese product. Generally, about 3 to about 30 percent of the proteins in the treated dairy liquid have been cross-linked. Generally, it is preferred that the proteins are cross-linked to form predominately dimers and other relatively low molecular weight homo- or hetero-oligomers (i.e., conjugates having molecular weights less than about 400,000 Daltons and preferably less than about 300,000 Daltons).

Figure 1:
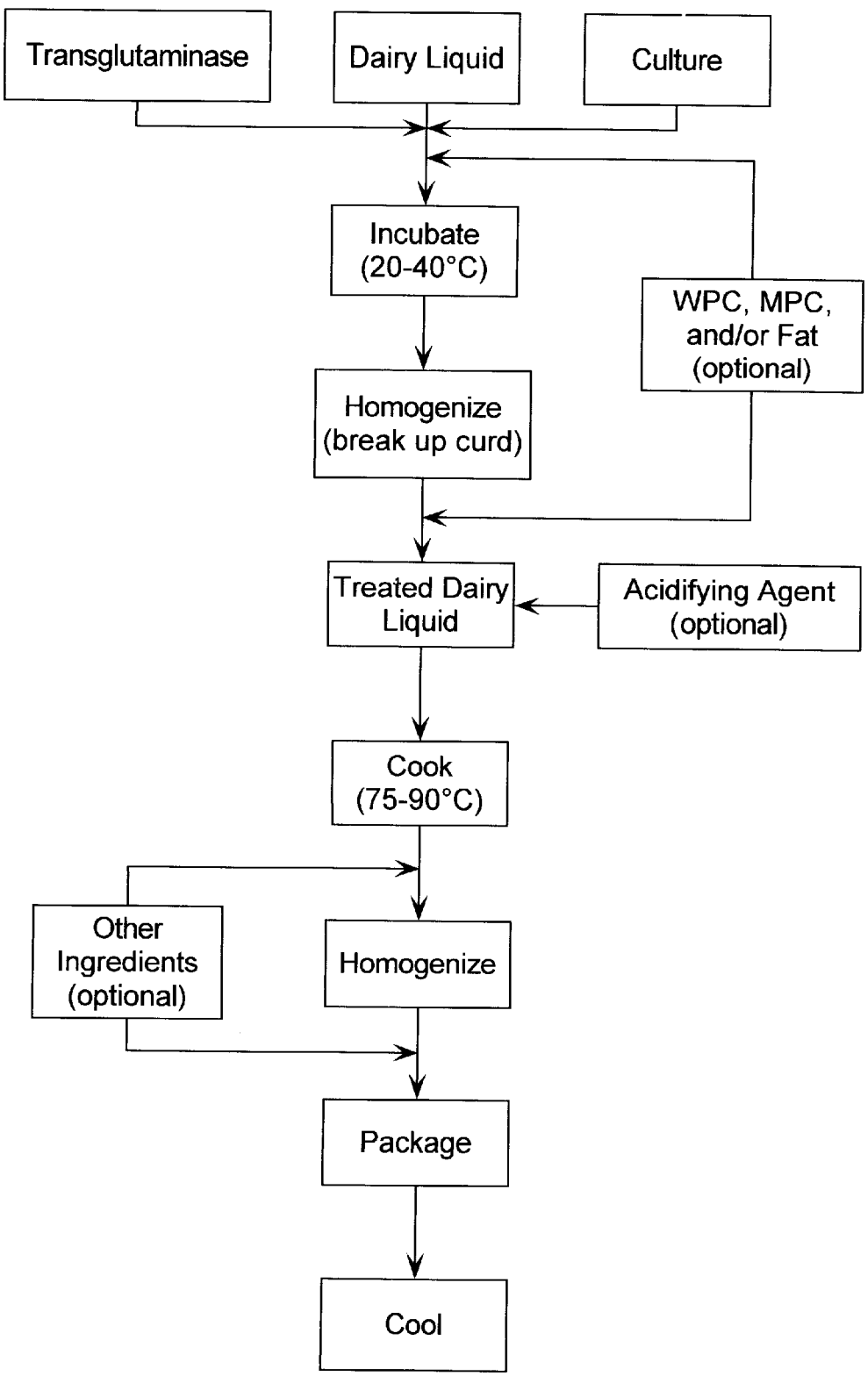
FIG. 1 provides a flow diagram illustrating one general embodiment of the process of the present invention.

FIG. 1 illustrates one embodiment of the process of the present invention. A dairy liquid, preferably pasteurized, is treated or incubated with transglutaminase and a lactic acid producing culture at about 20 to about 40° C., preferably about 25 to about 40° C., until the pH reaches about 4.2 to about 5.2 to cross-link at least a portion of the dairy proteins and to form a first dairy mixture. Whey protein concentrate, milk protein concentrate, fat, and/or water (i.e., dairy protein supplements) may be added to the dairy liquid before or after incubation in order to standardize or adjust the protein and fat contents to desired levels. After incubation, the mixture is treated with shear or by homogenization to break up curd formed during incubation and to produce a relatively homogenous slurry (i.e., the treated dairy liquid). If desired or appropriate, an edible acid may be added to the treated dairy liquid to adust the pH to a desired level. The treated dairy liquid is then cooked at about 75 to about 90° C. in order to irreversibly denature the proteins to form a denatured protein matrix stabilized emulsion system. Cross-linking via the transglutaminase will occur during both the incubation and cooking periods. Generally, cooking is continued for about 2 to about 120 minutes and preferably for about 10 to about 60 minutes. After cooking, the mixture is homogenized to reduce the average diameter of the fat globules to about 0.2 to about 3 microns, preferably to about 0.2 to about 1 microns, to form the desired cream cheese. If desired, optional ingredients (e.g., spices, flavorants, colorants, condiments, and the like) can be added before or after homogenization. Generally, it is preferred to add flavorants, colorants, and like before homogenization so that they are dispersed homogeneously throughout the final product; condiments (e.g., chives, scallions, and the like) are preferably added after homogenization to maintain their integrity in the final product. The cream cheese product is then packaged and cooled using conventional techniques.

Figure 2:
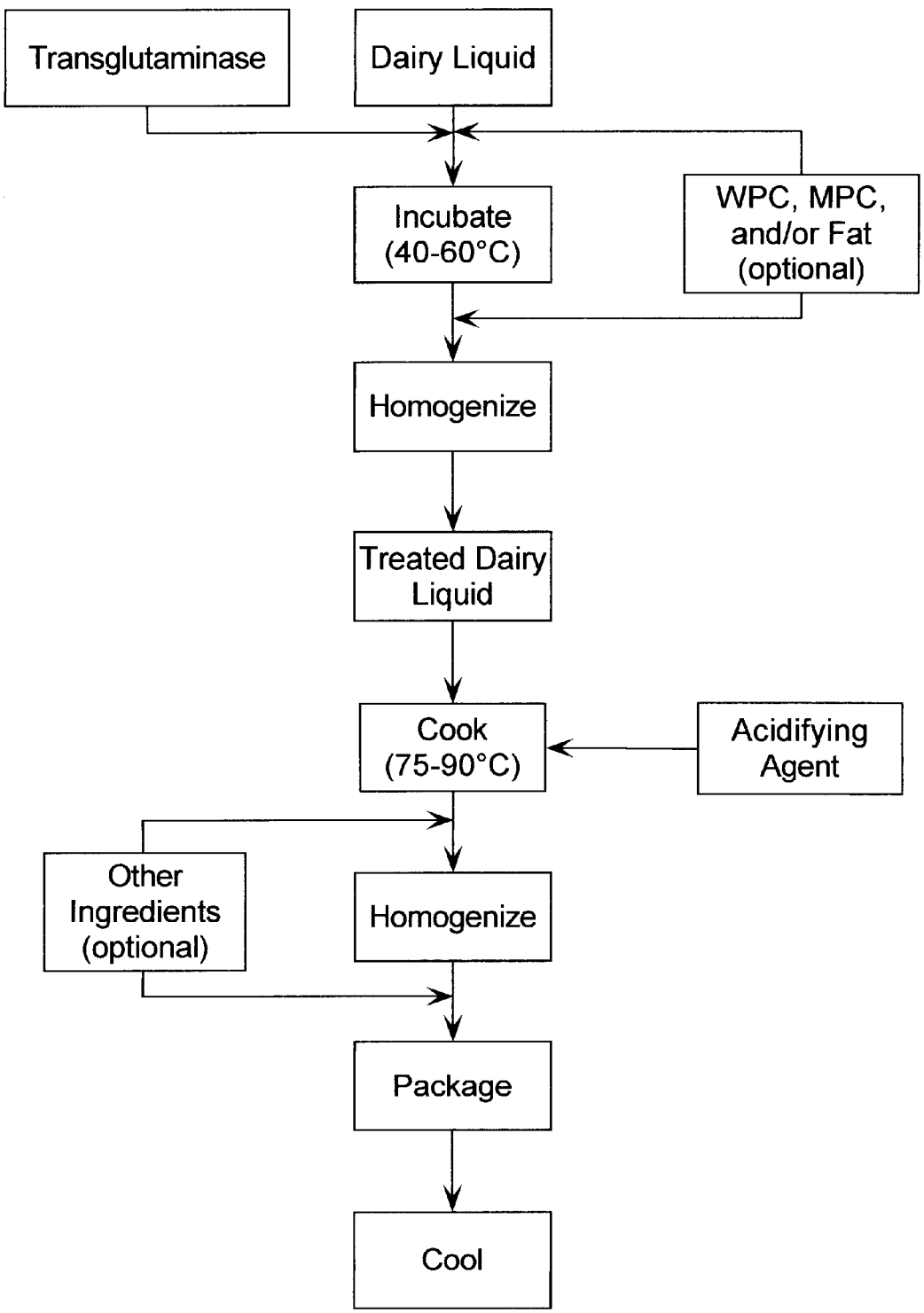
FIG. 2 provides a flow diagram illustrating another general embodiment of the process of the present invention.

FIG. 2 illustrates another embodiment of the present invention. A dairy liquid, preferably pasteurized, is treated or incubated with transglutaminase at about 40 to about 60° C. to cross-link at least a portion of the dairy proteins and to form a treated dairy liquid. Whey protein concentrate, milk protein concentrate, fat, and/or water (i.e., dairy protein supplements) may be added to the dairy liquid before or after incubation in order to standardize or adjust the protein and fat contents to desired levels. After incubation, the treated dairy liquid is homogenized and cooked at about 75 to about 90° C. in order to denature the proteins. Cross-linking via the transglutaminase will occur during both the incubation and cooking periods. Generally, cooking is continued for about 2 to about 120 minutes and preferably for about 10 to about 60 minutes. After cooking, the mixture is homogenized to reduce the average diameter of the fat globules to about 0.2 to about 3 microns, preferably to about 0.2 to about 1 microns, to form the desired cream cheese. If desired, optional ingredients (e.g., spices, flavorants, colorants, condiments, and the like) can be added before or after homogenization. Generally, it is preferred to add flavorants, colorants, and like before homogenization so that they are dispersed homogeneously throughout the final product; condiments (e.g., chives, scallions, and the like) are preferably added after homogenization to maintain their integrity in the final product. The cream cheese product is then packaged and cooled using conventional techniques.

Figure 3:
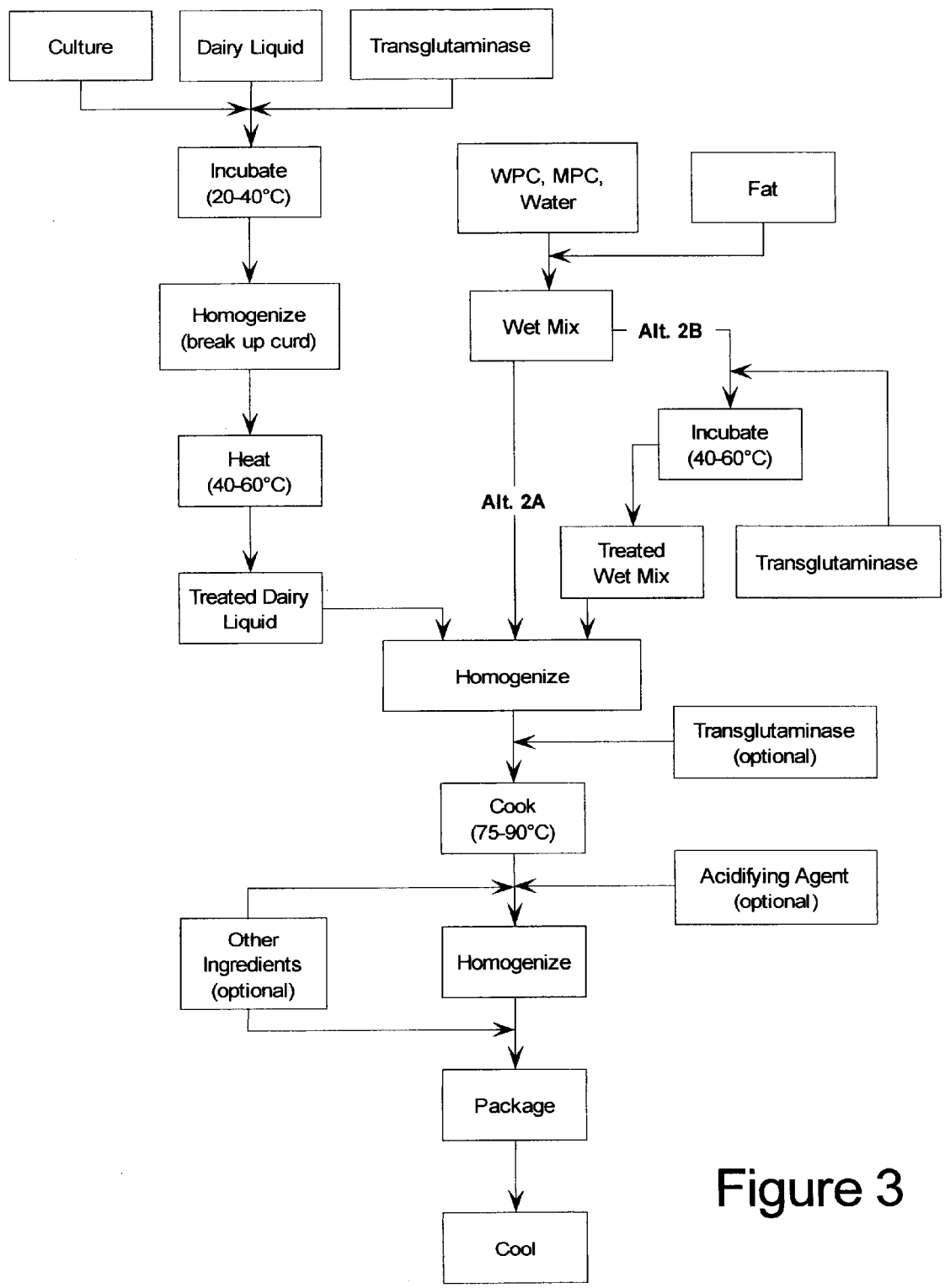
FIG. 3 provides a flow diagram illustrating one general embodiment of the process of the present invention.

FIG. 3 illustrates another embodiment of the present invention. This embodiment is similar to that illustrated in FIG. 1 except that a wet mix or a treated wet mix containing additional milk protein is added to the treated dairy liquid prior to the cooking step. A dairy liquid, preferably pasteurized, is treated or incubated with transglutaminase and a lactic acid producing culture at about 20 to about 40° C., preferably about 25 to about 40° C., until the pH reaches about 4.2 to about 5.2 to cross-link at least a portion of the dairy proteins and to form a first dairy mixture. After incubation, the mixture is treated with shear, preferably relatively gentle shear, to break up any curd that may have formed during incubation and to produce a relatively homogenous slurry. The homogenous slurry is then heated to about 40 to about 60° C. for about 2 to about 120 minutes, preferably about 10 to 60 minutes, to form the treated dairy liquid. The treated dairy liquid is then mixed with either the wet mix or the treated wet mix and then cooked at about 75 to about 90° C. in order to denature at least a portion of the proteins. Generally, the cooked blend is formed from about 50 to about 90 percent of the treated dairy liquid and about 10 to about 50 percent of the wet mix or treated wet mix. Generally, cooking is continued for about 2 to about 120 minutes and preferably for about 10 to about 60 minutes. If desired, additional cross-linking can be effected during the cooking step by addition of additional transglutaminase. If appropriate, the pH can be adjusted to the desired level by the addition of an edible acid. After cooking, the mixture is homogenized to reduce the average diameter of the fat globules to about 0.2 to about 3 microns, preferably to about 0.2 to about 1 microns, to form the desired cream cheese. If desired, optional ingredients (e.g., spices, flavorants, colorants, condiments, and the like) can be added before or after homogenization. Generally, it is preferred to add flavorants, colorants, and like before homogenization so that they are dispersed homogeneously throughout the final product; condiments (e.g., chives, scallions, and the like) are preferably added after homogenization to maintain their integrity in the final product. The cream cheese product is then packaged and cooled using conventional techniques.

Figure 4:
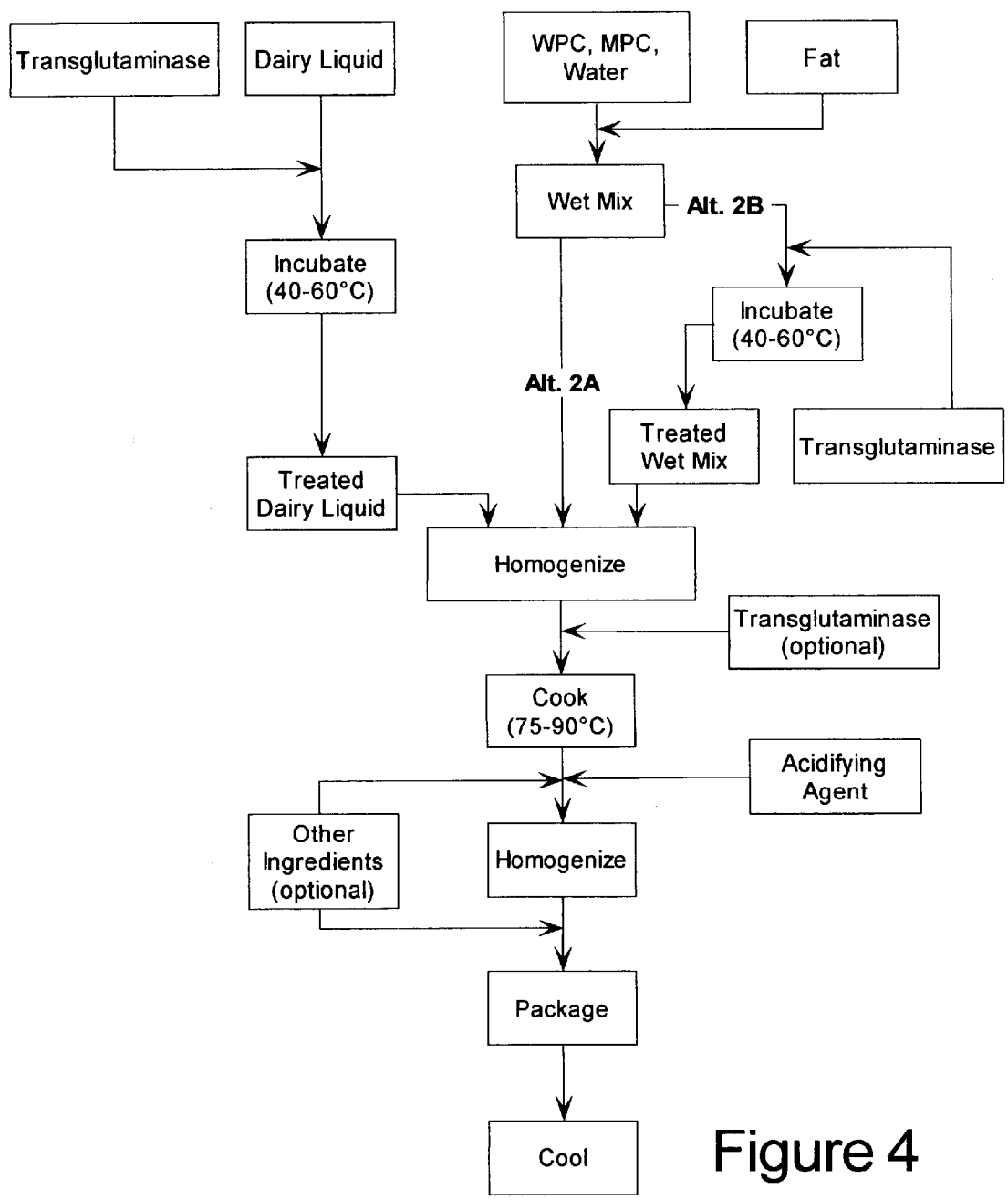
FIG. 4 provides a flow diagram illustrating another general embodiment of the process of the present invention.

FIG. 4 illustrates another embodiment of the present invention. This embodiment is similar to that illustrated in FIG. 2 except that a wet mix or a treated wet mix containing additional milk protein is added to the treated dairy liquid prior to the cooking step. A dairy liquid, preferably pasteurized, is treated or incubated with transglutaminase at about 40 to about 60° C. to cross-link at least a portion of the dairy proteins and to form a treated dairy liquid. After incubation, the treated dairy liquid is mixed with either the wet mix or the treated wet mix and then cooked at about 75 to about 90° C. in order to denature at least a portion of the proteins. Generally, the cooked blend is formed from about 50 to about 90 percent of the treated dairy liquid and about 10 to about 50 percent of the wet mix or treated wet mix. Generally, cooking is continued for about 2 to about 120 minutes and preferably for about 10 to about 60 minutes. If desired, additional cross-linking can be effected during the cooking step by addition of additional transglutaminase. If appropriate, the pH can be adjusted to the desired level by the addition of an edible acid. After cooking, the mixture is homogenized to reduce the average diameter of the fat globules to about 0.2 to about 3 microns, preferably to about 0.2 to about 1 microns, to form the desired cream cheese. If desired, optional ingredients (e.g., spices, flavorants, colorants, condiments, and the like) can be added before or after homogenization. Generally, it is preferred to add flavorants, colorants, and like before homogenization so that they are dispersed homogeneously throughout the final product; condiments (e.g., chives, scallions, and the like) are preferably added after homogenization to maintain their integrity in the final product. The cream cheese product is then packaged and cooled using conventional techniques.

The wet mix in FIGS. 3 and 4 is formed by mixing appropriate amounts of whey protein concentrate, milk protein concentrate, fat, and/or water (i.e., dairy protein supplements) to achieve the desired levels of fat and protein in the final cream cheese product. Preferably, the fat is melted prior to addition to the other ingredients to form the wet mix. If desired, the wet mix can be cross-linked using a transglutaminase treatment at about 40 to about 60° C. for about 2 to about 120 minutes, preferably about 10 to about 60 minutes. Preferably about 3 to about 30 percent of the proteins in the treated wet mix are cross-linked. The use of such a treated wet mix allows further control of the firmness of the final cream cheese product. Generally, the composition formed by blending the treated dairy liquid with the wet mix or treated wet mix contains about 50 to about 90 percent treated dairy liquid and about 10 to about 50 percent wet mix or treated wet mix.

The milk-based starting material for processes of the current invention is a dairy liquid containing dairy proteins. The dairy liquid, typically a mixture of dairy ingredients used to make cream cheese, comprises a dairy liquid or a processed dairy liquid, and normally has a butterfat content of from about 1 to about 20 percent, and preferably about 10 to about 14 percent.

As used herein, "dairy liquid" refers to milk, milk products obtained by fractionation of raw milk to provide a liquid fraction, or a solid milk fraction that is reconstituted to a liquid. For example, the milk may be treated to remove some or all of the butterfat, providing low fat milk or skim milk, respectively. Furthermore, whole milk, low fat milk, or skim milk may be concentrated by methods such as evaporation, ultrafiltration (with or without diafiltration), and the like. Evaporation provides dairy liquids containing a higher concentration of all the nonvolatile components; ultrafiltration provides dairy liquids with a higher concentration of the components that do not permeate the ultrafiltration membrane. In any case, the dairy proteins (including casein and whey protein) are retained, such that their concentrations in the resulting liquid is increased. Furthermore any of the above dairy liquids may be evaporated to dryness, providing milk solids originating from whole milk, low fat milk, or skim milk, and including casein, whey proteins, and lactose. Any of these solids may be reconstituted by the addition of water or a suitable aqueous composition (e.g., milk or a milk fraction). Reconstitution of dry milk thus provides dairy liquids that in general may have a broad range of final concentrations of the dairy proteins, lactose, butterfat, and other components. All the above liquids are included in the designation of "dairy liquids" as used herein. The dairy liquids employed in the present invention may originate from any lactating livestock animal whose milk is useful as a source of human food. Such livestock animals include, by way of nonlimiting example, cows, buffalo, other ruminants, goats, sheep, and the like. Generally, however, cows' milk is the preferred dairy liquid used in the practice of the invention.

As used herein, "casein" relates to any, or all, of the phosphoproteins in milk, and to mixtures of any of them. An important characteristic of casein is that it forms micelles in naturally occurring milk and in the dairy liquids employed in the present invention. Many casein components have been identified, including, but not limited to, α-casein (including $\alpha_{s1}$-casein and $\alpha_{s2}$-casein), β-casein, κ-casein, and their genetic variants.

As used herein, "whey protein" relates to the proteins contained in the dairy liquid (i.e., whey) obtained as a supernatant of the curds when milk or a dairy liquid containing milk components are curded to produce a cheese-making curd as a semisolid. Whey protein is generally understood to include principally the globular proteins β-lactoglobulin and α-lactalbumin. It may also include significantly lower concentrations of immunoglobulin and other globulins/albumins.

In certain embodiments, the dairy liquid can be provided by a process comprising: (a) providing an initial dairy liquid; (b) processing the initial dairy liquid to form a processed initial dairy liquid; and (c) adding a supplement to the processed initial dairy liquid to form the dairy liquid, wherein the supplement is selected from a source of dairy proteins, a source of fat, and both a source of dairy proteins and a source of fat. The source of dairy proteins added as a supplement typically includes a concentrated dairy protein source. As used herein a "concentrated dairy protein source" is a protein source wherein proteins are at, or can be reconstituted to be at, a concentration that is greater than the dairy liquid from which they originated. Examples of concentrated dairy protein sources include, but are not limited to, whey protein concentrate and milk protein concentrate, or combination of whey protein concentrate and milk protein concentrate. Typically, for whey protein concentrate and milk protein concentrate, protein concentrations are at least about 34 percent. Additionally, dairy protein supplements may include other sources of dairy proteins, such as whey proteins, that are not concentrated.

The fat source is typically a dairy fat source, preferably cream or butter fat. The fat source is typically added when the concentration of fat in the dairy liquid and concentrated dairy protein source, when used, is lower than desired to obtain the texture and body of cream cheese.

In embodiments which include a culturing step, including embodiments incorporating a combined culturing and cross-linking step (as described below and illustrated in FIGS. 1 and 3), culturing is typically carried out until the pH of the dairy liquid is reduced to about 4.2 to about 5.2, preferably about 4.4 to about 4.8, most preferably about 4.5 to about 4.7. Typically, the culturing and cross-linking are carried out for between 1 and about 24 hours at temperatures of between about 20 and 40° C. Preferably, the culturing and cross-linking time is from about 12 to about 24 hours at temperatures of about 25 to about 30° C. In one embodiment, the culturing and cross-linking is carried out for about 17 hours at a temperature of about 20 to about 30° C. Typically, the culturing step, including embodiments incorporating a combined culturing and cross-linking step, is done without disturbing the dairy liquid being cultured (i.e., without significant agitation).

As is well known in the art, the lactic acid-producing culture can be added as a starter culture. The starter culture is typically established by inoculating a lactic acid-producing bacteria into a relatively small quantity of dairy liquid compared to the quantity to be used in the cheese production process. The culture is incubated at a temperature that supports multiplication of the bacteria before being used to inoculate the full volume of dairy liquid for the batch of cheese production.

In certain embodiments, following the step of incubating the inoculated dairy liquid, the dairy liquid is heated and/or sheared. The heating is typically carried out between about 40 and 90° C. and an incubation time of between about 1 and about 60 minute. Preferably, the heating is carried out at a temperature of between about 50 and 82° C. and an incubation time of about between about 2 and 30 minutes. Shearing is typically carried out by homogenizing according to the methods described in the following section, or equivalent methods.

Homogenization is an important aspect of the current invention, and, therefore, may be performed at many different steps of the process of the current invention. The importance of homogenization is that it is used in the process of the current invention to create and maintain emulsions from the various liquids of the process and to maintain the various liquids in an emulsified state rather than a curded state. Not to be limited by theory, it is believed that a denatured protein matrix stabilized emulsion system is created as a result of the transglutaminase cross-linking as well as the homogenizing and heating steps, that gives the final product of the process the texture and body of cream cheese.

In certain steps, the homogenization can be accomplished by the use of shearing forces. In other embodiments, the shearing may or may not include homogenization. Typically, the dairy liquid is mixed to form a uniform substantially homogeneous mixture before proceeding to subsequent steps. In certain embodiments, after adding the source of milk proteins and the source of fat to the initial dairy liquid to form the dairy liquid, the dairy liquid is sheared with fat to form an emulsion of the supplemented dairy liquid.

Homogenization methods are well known in the food sciences. Homogenization is typically carried out at increased pressures. However, any effective homogenization method that can be used to homogenize dairy liquids can be used with the current invention. For example, but not intended to be limiting, a two-stage homogenizer may be used. Preferably, the first stage is operated at a pressure of about 2000 to about 10000 psi, preferably about 3000 to about 6000 psi, and the second stage at about 100 to about 1000 psi, preferably about 300 to about 1000 psi. Typically, where two or more homogenization steps are performed during the process, the first homogenization step is carried out at a lower shear force than subsequent homogenization steps.

The final homogenization is used to obtain the desired fat globule particle size in the final product. Particle size can be monitored using convention techniques, such as, for example, a laser scattering particle size distribution analyzer, and the like. Typically, fat particles in the final cream cheese product have average diameters from about 0.2 to about 3 microns, and preferably from about 0.2 to about 1 microns.

The final cooking is effective for conditioning (i.e., denaturing the proteins) the homogenized dairy product such that when cooled, a cream cheese product is obtained. Typically cooking is carried out at a temperature between about 70 and 95° C. for about 2 and about 120 minutes and preferably at a temperature between about 75 and 90° C. for about 10 and 60 minutes. Undercooking generally results in a too soft and unstable product, whereas overcooking generally produces a undesired (e.g., grainy) texture.

The current invention includes adding an effective amount of an acidifying agent. The acidifying agent may be either a food grade acidulent (FIGS. 2 and 4) or a lactic acid-producing culture (FIGS. 1 and 3), both of which are well known in the art of cheese manufacturing. Food grade acidulents, include, but are not limited to citric acid, lactic acid, phosphoric acid, acetic acid or vinegar, and the like. Preferably, the acidifying agent is a lactic acid source, such as a lactic acid solution or a lactic-acid producing culture. An effective amount of an acidifying agent is one that brings the final pH of the process solution to which it is added to a pH of between about 4.0 and about 6.0, preferably about 4.5 and about 5.5, most preferably to about 4.9 and about 5.2.

In preferred embodiments of the current invention, the acidifying agent is a lactic acid-producing culture (see FIGS. 1 and 3). Such cultures are well known in the art of food science. Any lactic acid-producing bacteria used in conventional cream cheesemaking can be used in the process of the current invention. Not to be limited by theory, as is known in the art, lactic acid-producing microbes are used in cheese manufacturing to ferment lactose present in the dairy liquid and to cause further decomposition of the clotted casein into smaller peptides and free amino acids as a result of the culture's production of proteases and peptidases. The lactic acid-producing culture may be added in amounts which are conventional for the present purpose (i.e., typically about 10,000 to 100,000 bacteria/g of dairy liquid). The cultures may be added as freeze-dried, frozen, or liquid cultures. If appropriate, an additional acidifying agent, such as a solution of lactic acid, may be added to bring the pH within the final target range.

Cross-linking of proteins during the process of the current invention is catalyzed by transglutaminase. Typically, the degree of cross-linking is determined by analyzing the texture and protein retention characteristics of processed samples. In one method for determining effective conditions for cross-linking (e.g., incubation temperature, time, concentration of transglutaminase), diminution of major bands on SDS-PAGE gels is determined. Transglutaminase is typically added to process liquids that contain high protein concentrations in the process of the current invention. As shown in FIGS. 3 and 4, multiple transglutaminase treatments can be used. Preferably transglutaminase is added to emulsified process liquids. Therefore, there is typically a homogenization step to emulsify the process liquid before transglutaminase is added. Typically, for example, the cross-linking may be carried out for between about 2 and 120 minutes at a temperature of between about 40 and 60° C., preferably between about 10 and 60 minutes at a temperature between about 45 and 55° C. In other embodiments, the cross-linking is carried out in a combined culturing and cross-linking step as described above.

Transglutaminases are enzymes which catalyze the transfer of the $\gamma$-carboxamide group of a glutaminyl residue in a protein or peptide to the $\epsilon$-amino of a lysyl residue of the same or a different protein or peptide, thereby forming a $\gamma$-carboxyl-$\epsilon$-amino cross-link. Transglutaminases have a broad occurrence in living systems, and may be obtained, for example, from microorganisms such as those belonging to the genus Streptoverticillium, from *Bacillus subtilis*, from various Actinomycetes and Myxomycetes, from fish species and other marine sources, from plant sources, and from animal sources, especially mammals. Mammals provide the blood clotting protein activated Factor XIII and liver transglutaminase obtained, for example, from pigs. In general, transglutaminase from animal sources require calcium ions for activity. Recombinant forms of transglutaminase enzymes may be obtained by genetic engineering methods as heterologous proteins produced in bacterial, yeast, and insect or mammalian cell culture systems. The principal requirement of any transglutaminase employed in the instant invention is that it has the desired cross-linking activity. Any enzyme having such transglutaminase activity may be employed in the methods of the present invention. In a preferred embodiment, the transglutaminase is obtained from the genus Streptoverticillium.

Transglutaminase activity may be determined using known procedures. One such colorimetric procedure uses benzyloxycarbonyl-L-glutaminyl-glycine and hydroxylamine to form a ($\gamma$-carboxyl-hydroxamic acid if transglutaminase is present. An iron complex of the hydroxamic acid can be formed in the presence of ferric chloride and trichloroacetic acid. Using the absorbance at 525 nm with appropriate standards, the activity of enzyme present may be determined (see, e.g., U.S. Pat. No. 5,681,598; and *J. Biol. Chem.* 240:2951 (1965)).

In certain embodiments, transglutaminase is used at concentrations of less than 10 international units (IU) per gram of dairy liquid, preferably less than 5 IU per gram, more preferably less than 1 IU per gram of dairy liquid. In certain embodiments, transglutaminase is used at a concentration of about 0.4 to about 0.8 IU per gram of dairy liquid or supplemented dairy liquid.

In certain embodiments of the process of the current invention (see, e.g., FIGS. 1 and 3), the dairy liquids are cultured and cross-linked during a combined culturing and cross-linking step by the addition of an acidifying agent and transglutaminase. Typically in these embodiments involving a combined culturing and cross-linking step, transglutaminase is added to the dairy liquid as soon as the acidifying agent is added (within 1 hour of addition of the acidifying agent, more typically, within 10 minutes of addition of the acidifying agent, most typically, immediately after addition of the acidifying agent). Delayed addition of transglutaminase results in a lesser degree, of cross-linking with the same enzyme dosage. For these embodiments involving a combined culturing and cross-linking step, typically the acidifying agent is a lactic acid-producing bacteria.

The resulting cream cheese product is typically cooled following the process of the current invention using conventional techniques. Typically, the conditioned dairy product is cooled after it is hot filled. The temperature of filling is typically about 50 to about 70° C. Typically, the cream cheese is hot filled directly into a container (e.g., cup, tub, and the like) suitable for retail sale and then sealed. Procedures for filling cream cheese are well known in the art.

For the current invention, stabilizers are not necessary to obtain the texture and/or body of cream cheese. However, stabilizers may be included in cream cheese made according to the current invention. Examples of stabilizers include gums such as locust bean gum, guar gum, xanthan gum, gum arabic, and the like; cellulose derivatives such as finely divided cellulose and carboxymethylcellulose; starch such as corn starch, rice starch, potato starch, tapioca starch, wheat starch and sweet potato starch; and modified starch such as phosphorylated starch.

Other ingredients may be incorporated into the cream cheeses prepared by the present processes. For example, calcium may be added for calcium fortification. Suitable calcium sources include, for example, calcium chloride, calcium sulfate, calcium phosphate, calcium citrate, and the like. Flavorings such as butter flavor, milk flavor, cheese flavor, and the like, various seasonings, fruit purees, and/or fruit powders may also be used for flavorings. For the purpose of sweetening, mono and oligosaccharides such as sucrose glucose, fructose, or maltose; sugar alcohols such as sorbitol, maltitol and lactitol; and low-calorie sweeteners such as saccharin, aspartame, stevioside, and thaumatin may be used. Colorings such as, for example, β-carotene, annatto, and the like may also be used. Such other ingredients that can be used in the process of manufacturing cream cheese according to the current invention should not, of course, interfere with transglutaminase activity so as to completely inhibit the ability of this enzyme to cross-link proteins found in dairy liquids. Preferably, therefore, such optional ingredients are preferably added to the cream cheese after cross-linking has been completed as illustrated in FIGS. 1–4. Generally, conventional milk clotting or renneting enzymes are not used in the processes of the current invention.

In another aspect, the current invention relates to wheyless cream cheese products, produced by a process as described above, including any of the embodiments described above. The cheese products of the current invention have a number of advantages. For example, the wheyless cream cheese products have the texture and body of traditional cream cheese but have reduced syneresis. Conventional cream cheese is a acid-coagulated curd system with its firmness determined by protein (mainly caseins) concentration as well as denatured casein micelles. Consequently, conventional cream cheese requires a relatively higher protein concentration in order to maintain its firmness and minimize the rate of syneresis. Syneresis in conventional cream cheese can be described as a secondary curding process of casein micelles. Because all casein molecules are relatively unstructured (i.e., flexible), even denatured casein molecules still have the tendency to form more compact micelle structures, resulting in syneresis (i.e., the release of absorbed water or whey). As hydrophobic interactions are the main force involved in the formation of casein micelles, the rate of syneresis increases with increasing temperature (i.e., stronger hydrophobic interaction at higher temperature). In the present invention, the structure and firmness of the final product is not determined by caseins since the caseins present are mostly cross-linked. Thus, such limitations as those found in conventional cream cheese are minimized or essentially eliminated. Moreover, protein conjugates formed from transglutaminase catalyzed cross-linking increase stability of the emulsion system and water absorption capacity, so that the syneresis of products can be minimized.

The following examples describe and illustrate the processes and products of the invention. These examples are intended to be merely illustrative of the present invention, and not limiting thereof in either scope or spirit. Unless indicated otherwise, all percentages and ratios are by weight. Those skilled in the art will readily understand that variations of the materials, conditions, and processes described in these examples can be used.

EXAMPLE 1

Production of Wheyless Cream Cheese Using Transglutaminase and a Lactic Acid Producing Culture This example illustrates the process of the present invention from FIG. 3 using Alternative 2A. A cream cheese was prepared using the following process:

(1) Whole milk was pasteurized at 80° C. for 18 seconds and cooled to 25° C. to form the dairy liquid;

(2) The dairy liquid (25.4 kg) was inoculated with 20 g of lactic acid producing culture (Hansen CHN 12; Chr. Hansen, Milwaukee, Wis.) at 25° C.;

(3) Transglutaminase (TG-TI with an activity of about 100 IU/g; 14 g dissolved in 100 g of water) from Ajinomoto U.S.A., Inc. (Paramus, N.J.) was added to the inoculated dairy liquid;

(4) The resulting mixture was cultured by quiescent incubation at about 25° C. for about 17 hours to lower pH to about 4.5;

(5) After breaking up the curd, the resulting mixture was heated to about 60° C. to form the treated dairy liquid;

(6) A wet mix containing milk protein concentrate (0.42 kg; MPC NZ 70), whey protein concentrate (1.39 kg; WPC AMP 800), hot water (3.86 kg; about 60° C.), and anhydrous butter fat (7.05 kg) was prepared and then added to, and mixed with, the treated dairy liquid;

(7) The resulting solution was homogenized in two stages (i.e., about 3000 psi in the first stage and about 500 psi in the second stage) to produce an emulsion;

(8) The emulsion was heated to 86° C. and incubated for 30 minutes in order to irreversibly denature the proteins;

(9) Lactic acid (95.0 g of an 88 percent solution) was added to adjust the pH to about 5 and the solution was mixed and homogenized using a two-stage homogenizer operating at about 3000 psi in the first stage and about 500 psi in the second stage to form the cream cheese having fat globules with an average particle diameter of about 0.2 to about 1 microns; and

(10) The cream cheese was hot filled into cups which were sealed and stored at 4° C. for further evaluation.

Control samples were prepared using a process identical to that described above except that no transglutaminase was used. Moisture contents were determined using a microwave oven at an 80 percent power level. Viscosities were measured at 4° C. using a Viscometer Model HAAKE VT550 (HAAKE Inc., Karlsruhe, Germany).

Syneresis was measured after a 4 hour incubation at 25° C. by determining the amount of moisture phase separated from the sample during the incubation period. The cheese sample in an 8 oz. cup was cut in the middle and half of the sample removed and its weight measured. After incubation the moisture phase was removed and the net change in weight was the amount of moisture separated. The rate of syneresis was determined as the net change in weight divided by the original weight of the sample after cutting.

The results are summarized in Table 1.

TABLE 1

Effect of Transglutaminase Cross-linking on Product Texture.

|  | Control | TG treated |
| --- | --- | --- |
| pH | 5.26 | 5.18 |
| Moisture (%) | 69.1 | 68.1 |
| Cold viscosity (Pa) | 802 | 1558 |
| Syneresis @ 25° C. for 4 hr (%) | 10.0 | 6.9 |

Based on the ingredients, the product should contain about 6.0 percent protein (with the ratio of WP/casein about 60/40), about 22 percent fat, and about 68 percent moisture. The invention cream cheese obtained had the taste, consistency, and appearance of cream cheese without isolation of curd from whey during processing. Viscosity of the transglutaminase-treated sample (1558 Pa) was much higher than that of the control sample (802 Pa), although it contained slightly less moisture (68.1 percent) than the control sample (69.1 percent). Treatment of milk with transglutaminase also reduced the rate of syneresis. Syneresis could also be reduced even further (data not shown), if desired, by incorporation of salt and/or a gum as optional ingredients at levels of about 0.1 to about 0.5 percent.

EXAMPLE 2
Effect of Transglutaminase Cross-linking on Product Texture Using a Non-Culturing Process This example illustrates the process of the present invention using the process illustrated in FIG. 2. A cream cheese was prepared using the following process:

(1) Whole milk (12.7 kg) was heated to about 64° C.;
(2) Milk protein concentrate (0.21 kg; MPC NZ 70), whey protein concentrate (0.70 kg; WPC AMP 800), melted anhydrous butter fat (2.8 kg), and hot water (2.1 kg; about 65° C.), were added to the heated milk and the solution was sheared to form an emulsion;
(3) Transglutaminase (the same as used in Example 1) was added to the sample in the amounts indicated in Table 2 and the samples were incubated at 50° C. for 60 min;
(4) The incubated sample was homogenized in two stages using 5000 psi in the first stage and 500 psi in the second stage to produce an emulsion;
(5) The emulsion was heated to 82° C. and held for 30 min;
(6) Lactic acid (78.0 g of an 88 percent solution) and salt (40 g) were added and mixed with the sample;
(7) The sample was then homogenized in two stages using 5000 psi in the first stage and 500 psi in the second stage; and
(8) The homogenized samples were hot filled into cups which were sealed and stored at 4° C. for further evaluation.

Control samples were prepared using a process identical to that described above except that no transglutaminase was added. No salts/gum were added to the samples for the process used in this Example. Moisture content, viscosity, and syneresis were measured as described in Example 1. Protein composition of curd and whey fractions were analyzed by Coomassie blue staining of proteins separated by electrophoresis on a 16.5% SDS polyacrylamide gel, according to the method of Laemmli, *Nature*, 227:680 (1970).

TABLE 2

Experimental Design.

| | Sample | | |
|---|---|---|---|
| Ingredient | A (Control) | B | C |
| Whole milk (kg) | 12.7 | 12.7 | 12.7 |
| MPC NZ 70 (kg) | 0.21 | 0.21 | 0.21 |
| WPC 800 (kg) | 0.70 | 0.70 | 0.70 |
| Anhydrous butter fat (kg) | 2.8 | 2.8 | 2.8 |
| Hot water (about 60° C.) (kg) | 2.1 | 2.1 | 2.1 |
| Transglutaminase | 0 | 50 | 100 |

Figure 5:
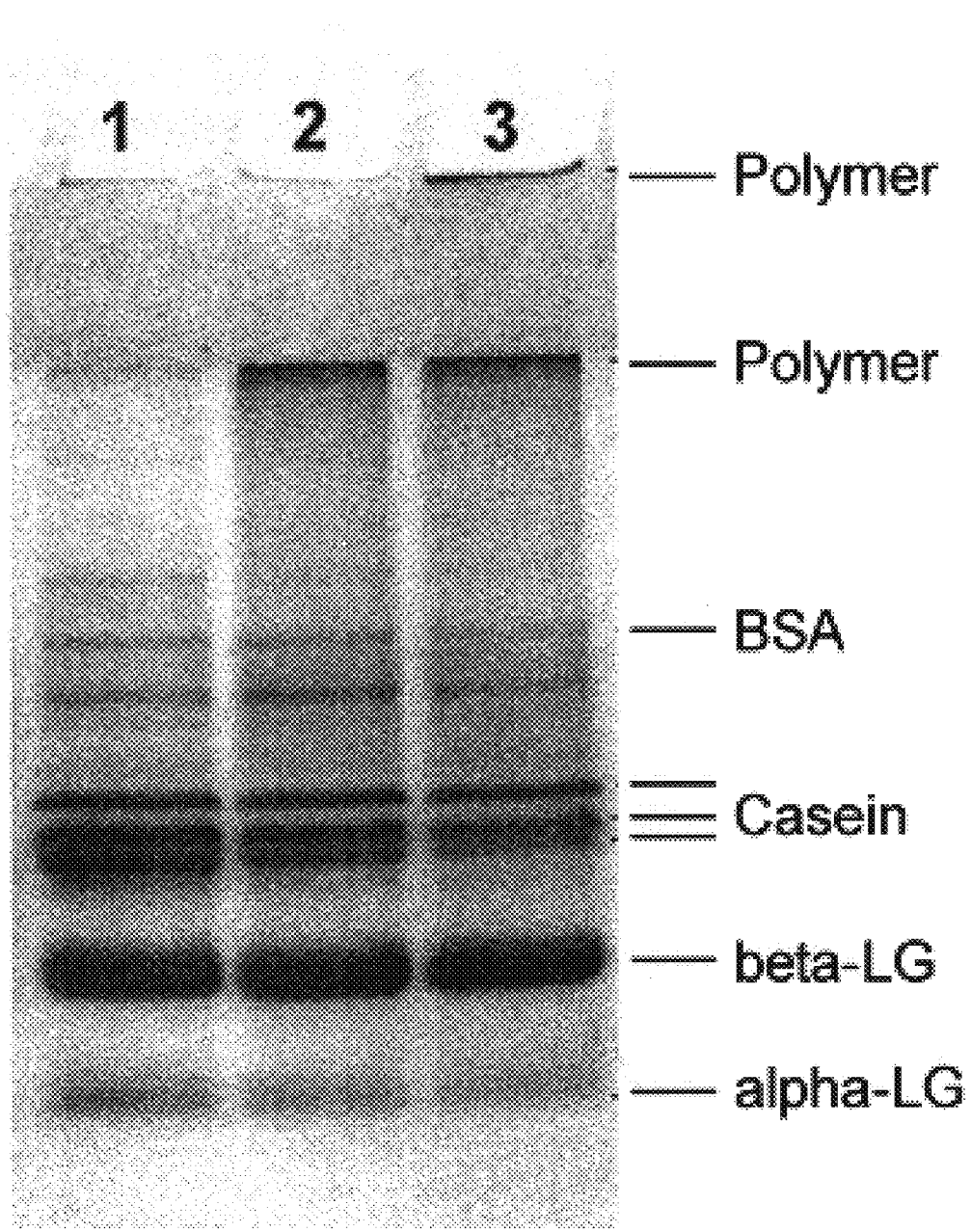
FIG. 5 is a Coomassie-stained 16.5% Tricine-SDS PAGE gel with the following samples: Lane 1: Control sample prepared using a process that did not include transglutaminase treatment; Lane 2: Sample prepared using a process that included treatment with 50 g of transglutaminase; Lane 3: Sample prepared using a process that included treatment with 100 g of transglutaminase. All non-control samples were prepared by the process illustrated in FIG. 2 and Example 2; the control sample was prepared using a similar process except that transglutaminase was not used.

The process used to produce cheese for this experiment is shown in diagrammatically in FIG. 2. The process described in this example produced a product with the taste, consistency, and appearance of cream cheese without the isolation of curd from whey during processing. The transglutaminase treatment (i.e., cross-linking of proteins) had significant effects on the viscosity and rate of syneresis of prototypes obtained (Table 3). The viscosity of transglutaminase-added products was greater than that of control samples. With treatment of 50 g of transglutaminase for 60 min, the cold viscosity of the finished product (Sample B) was almost twice that of the control sample. However, increased transglutaminase dosage, which results in more extensive cross-linkage of proteins, did not further increase the viscosity of the product (Sample C). As shown in FIG. 5, increased transglutaminase dosage generated more highly cross-linked protein polymers that could not enter the stacking gel. Those very high molecular weight protein polymers do not appear to be effective for improving the quality of product.

TABLE 3

Effect of Transglutaminase Cross-linking on Product Texture.

| | Sample | | |
|---|---|---|---|
| Product Properties* | A (Control) | B | C |
| pH | 5.4 | 5.3 | 5.3 |
| Moisture (%) | 67.2 | 66.9 | 67.8 |
| Cold viscosity (Pa) | 2754 | 5080 | 4002 |
| Syneresis (25° C. for 3 h) (%) | 3.3 | 1.7 | 2.1 |

*Moisture of the samples was determined by microwave oven test at 80 percent power level. Data are mean values of triplicate measurements.

In addition to improving viscosity, the cream cheese produced by the process used in this experiment had reduced syneresis. In fact, the rate of syneresis for the sample treated with transglutaminase (sample B, Table 3) is about half of the control sample. Too high a degree of cross-linkage (Sample C, Table 3) resulted in an increased rate of syneresis, compared to that of the transglutaminase-treated sample (Sample B, Table 3).

In conclusion, the current Example describes a wheyless cream cheese process wherein transglutaminase treatment improved product firmness and minimized the rate of syneresis. Furthermore, there appeared to be an optimal degree of cross-linking which produced the best results. The degree of cross-linking should be sufficient to provide the desired textural and protein retention characteristics in the final cream cheese product. Generally, about 3 to about 30 percent of the proteins in the treated dairy liquid have been cross-linked. Generally, it is preferred that the proteins are cross-linked to form predominately dimers and other relatively low molecular weight homo- or hetero-oligomers (i.e., conjugates having molecular weights less than about 400,000 Daltons and preferably less than about 300,000 Daltons).

What is claimed is:

1. A process for making a wheyless cream cheese, said process comprising:
   (1) treating a dairy liquid containing dairy proteins with transglutaminase and a lactic acid producing culture at about 20 to about 40° C. until the pH reaches about 4.2 to about 5.2 to cross-link at least a portion of the dairy proteins and to form a first dairy mixture;
   (2) homogenizing the first dairy mixture to break up any curd that may have formed and to form a treated dairy mixture;
   (3) cooking the treated dairy mixture at about 75 to about 90° C. for about 2 to about 120 minutes to form a first blend; and
   (4) homogenizing the first blend to form a cream cheese having fat globules with an average diameter of about 0.2 to about 3 microns.

2. The process as defined in claim 1, wherein the fat globules have an average diameter of about 0.2 to about 1 microns.

3. The process as defined in claim 1, wherein about 3 to about 30 percent of the proteins in the treated dairy mixture have been cross-linked to form conjugates having molecular weights less than about 400,000 Daltons.

4. The process as defined in claim 2, wherein about 3 to about 30 percent of the proteins in the treated dairy mixture have been cross-linked to form conjugates having molecular weights less than about 400,000 Daltons.

5. The process as defined in claim 1, wherein the treated dairy liquid is standardized by adding whey protein concentrate, milk protein concentrate, fat, or mixtures thereof to either the dairy liquid or the treated dairy liquid.

6. The process as defined in claim 2, wherein the treated dairy liquid is standardized by adding whey protein concentrate, milk protein concentrate, fat, or mixtures thereof to either the dairy liquid or the treated dairy liquid.

7. A process for making a wheyless cream cheese, said process comprising:
   (1) treating a dairy liquid with transglutaminase at about 40 to about 60° C. for about 2 to about 120 minutes to cross-link at least a portion of the dairy proteins and to form a treated dairy liquid;
   (2) cooking the treated dairy mixture at 75 to about 90° C. for about 2 to about 120 minutes to form a first blend;
   (3) adjusting the pH of the first blend to about 4.2 to about 5.2 by adding an edible acid; and
   (4) homogenizing the pH-adjusted first blend to form the wheyless cream cheese having fat globules with an average diameter of about 0.2 to about 3 microns.

8. The process as defined in claim 7, wherein the fat globules have an average diameter of about 0.2 to about 1 microns.

9. The process as defined in claim 7, wherein about 3 to about 30 percent of the proteins in the treated dairy liquid have been cross-linked to form conjugates having molecular weights less than about 400,000 Daltons.

10. The process as defined in claim 8, wherein about 3 to about 30 percent of the proteins in the treated dairy liquid have been cross-linked to form conjugates having molecular weights less than about 400,000 Daltons.

11. The process as defined in claim 7, wherein the treated dairy liquid is standardized by adding whey protein concentrate, milk protein concentrate, fat, or mixtures thereof to the dairy liquid either before or after the transglutaminase treatment step.

12. The process as defined in claim 8, wherein the treated dairy liquid is standardized by adding whey protein concentrate, milk protein concentrate, fat, or mixtures thereof to the dairy liquid either before or after the transglutaminase treatment step.

13. A process for making a wheyless cream cheese, said process comprising:
   (1) blending a dairy liquid containing dairy proteins with transglutaminase and a lactic acid producing culture to form a first dairy mixture;
   (2) incubating the first dairy mixture at about 20 to about 40° C. until the pH reaches about 4.2 to about 5.2 to cross-link at least a portion of the dairy proteins and to form a second dairy mixture;
   (3) homogenizing the second dairy mixture to break up any curd that may have formed and to form a third dairy mixture;
   (4) heating the third dairy mixture at about 40 to about 60° C. for about 2 to about 120 minutes to form a treated dairy liquid;
   (5) mixing the treated dairy liquid with a wet mix or a treated wet mix to form a first blend;
   (6) homogenizing the first blend to form a second blend;
   (7) cooking the second blend at a temperature of about 75 to about 90° C. for about 2 to about 120 minutes to form a third blend; and
   (8) homogenizing the third blend to form a cream cheese having fat globules with an average diameter of about 0.2 to about 3 microns;
   wherein the wet mix is prepared by a first method comprising:
      (A) blending whey protein, milk protein concentrate, or mixtures thereof in water at a temperature of about 60 to about 75° C. to form a first mixture containing dairy proteins; and
      (B) blending fat with the first mixture to form the wet mix; and
   wherein the treated wet mix is prepared by a second method comprising:
      (A) homogenizing the wet mix;
      (B) adding transglutaminase to the homogenized wet mix to form a second mixture; and
      (C) incubating the second dairy mixture for a time and temperature sufficient to cross-link at least a portion of the dairy proteins to form the treated wet mix.

14. The process as defined in claim 13, wherein the first blend is formed from about 50 to about 90 percent of the treated dairy liquid and about 10 to about 50 percent of the wet mix.

15. The process as defined in claim 13, wherein the first blend is formed from about 50 to about 90 percent of the treated dairy liquid and about 10 to about 50 percent of the treated wet mix.

16. The process as defined in claim 13, wherein the fat globules have an average diameter of about 0.2 to about 1 microns.

17. The process as defined in claim 14, wherein the fat globules have an average diameter of about 0.2 to about 1 microns.

18. The process as defined in claim 15, wherein the fat globules have an average diameter of about 0.2 to about 1 microns.

19. The process as defined in claim 13, wherein about 3 to about 30 percent of the proteins in the treated dairy liquid have been cross-linked to form conjugates having molecular weights less than about 400,000 Daltons.

20. The process as defined in claim 14, wherein about 3 to about 30 percent of the proteins in the treated dairy liquid have been cross-linked to form conjugates having molecular weights less than about 400,000 Daltons.

21. The process as defined in claim 15, wherein about 3 to about 30 percent of the proteins in the treated dairy liquid have been cross-linked to form conjugates having molecular weights less than about 400,000 Daltons.

22. The process as defined in claim 14, wherein the treated dairy liquid is standardized by adding whey protein concentrate, milk protein concentrate, fat, or mixtures thereof to the wet mix.

23. The process as defined in claim 15, wherein the treated dairy liquid is standardized by adding whey protein concentrate, milk protein concentrate, fat, or mixtures thereof to the wet mix.

24. A process for making a wheyless cream cheese, said process comprising:
   (1) blending a dairy liquid containing dairy proteins with transglutaminase a first dairy mixture;

(2) incubating the first dairy mixture at about 40 to about 60° C. for about 2 to about 120 minutes to cross-link at least a portion of the dairy proteins to form a treated dairy mixture;
(3) mixing the treated dairy liquid with a wet mix or a treated wet mix to form a first blend;
(4) homogenizing the first blend;
(5) cooking the homogenized first blend at about 50 to about 95° C. for about 2 to about 120 minutes to form a second blend;
(5) adjusting the pH of the second blend to about 4.2 to about 5.2 by adding an edible acid to form a third blend; and
(6) homogenizing the third blend to form a cream cheese having fat globules with an average diameter of about 0.2 to about 3 microns;
wherein the wet mix is prepared by a first method comprising:
(A) blending whey protein, milk protein concentrate, or mixtures thereof in water at a temperature of about 60 to about 75° C. to form a first mixture containing dairy proteins; and
(B) blending fat with the first mixture to form the wet mix; and
wherein the treated wet mix is prepared by a second method comprising:
(A) homogenizing the wet mix;
(B) adding transglutaminase to the homogenized wet mix to form a second mixture; and
(C) incubating the second dairy mixture for a time and temperature sufficient to cross-link at least a portion of the dairy proteins to form the treated wet mix.

25. The process as defined in claim 24, wherein the first blend is formed from about 50 to about 90 percent of the treated dairy liquid and about 10 to about 50 percent of the wet mix.

26. The process as defined in claim 24, wherein the first blend is formed from about 50 to about 90 percent of the treated dairy liquid and about 10 to about 50 percent of the treated wet mix.

27. The process as defined in claim 24, wherein the fat globules have an average diameter of about 0.2 to about 1 microns.

28. The process as defined in claim 25, wherein the fat globules have an average diameter of about 0.2 to about 1 microns.

29. The process as defined in claim 26, wherein the fat globules have an average diameter of about 0.2 to about 1 microns.

30. The process as defined in claim 24, wherein about 3 to about 30 percent of the proteins in the treated dairy liquid have been cross-linked to form conjugates having molecular weights less than about 400,000 Daltons.

31. The process as defined in claim 25, wherein about 3 to about 30 percent of the proteins in the treated dairy liquid have been cross-linked to form conjugates having molecular weights less than about 400,000 Daltons.

32. The process as defined in claim 26, wherein about 3 to about 30 percent of the proteins in the treated dairy liquid have been cross-linked to form conjugates having molecular weights less than about 400,000 Daltons.

33. The process as defined in claim 25, wherein the treated dairy liquid is standardized by adding whey protein concentrate, milk protein concentrate, fat, or mixtures thereof to the wet mix.

34. The process as defined in claim 26, wherein the treated dairy liquid is standardized by adding whey protein concentrate, milk protein concentrate, fat, or mixtures thereof to the wet mix.

* * * * *

UNITED STATES PATENT AND TRADEMARK OFFICE
CERTIFICATE OF CORRECTION

PATENT NO.     : 6,416,797 B1
DATED          : July 9, 2002
INVENTOR(S)    : Han et al.

It is certified that error appears in the above-identified patent and that said Letters Patent is hereby corrected as shown below:

<u>Title page,</u>
Item [75], change "Evanston" to -- Penzoerg, Germany --.

Signed and Sealed this

Twenty-eighth Day of January, 2003

JAMES E. ROGAN
*Director of the United States Patent and Trademark Office*